United States Patent
Kantrowitz et al.

(10) Patent No.: US 9,498,647 B2
(45) Date of Patent: Nov. 22, 2016

(54) FIDUCIAL MARKER SYSTEM FOR SUBJECT MOVEMENT COMPENSATION DURING MEDICAL TREATMENT

(76) Inventors: Allen B. Kantrowitz, Williamstown, MA (US); In K. Mun, Nanuet, NY (US)

( * ) Notice: Subject to any disclaimer, the term of this patent is extended or adjusted under 35 U.S.C. 154(b) by 1319 days.

(21) Appl. No.: 11/534,759

(22) Filed: Sep. 25, 2006

(65) Prior Publication Data
US 2007/0106152 A1 May 10, 2007

Related U.S. Application Data

(60) Provisional application No. 60/720,244, filed on Sep. 23, 2005.

(51) Int. Cl.
*A61N 5/10* (2006.01)
*A61B 17/00* (2006.01)

(52) U.S. Cl.
CPC ............ *A61N 5/1049* (2013.01); *A61B 34/20* (2016.02); *A61B 90/36* (2016.02); *A61B 90/39* (2016.02); *A61B 90/98* (2016.02); *A61B 2017/00694* (2013.01); *A61B 2017/00699* (2013.01); *A61B 2034/2051* (2016.02); *A61B 2090/397* (2016.02); *A61N 5/1067* (2013.01)

(58) Field of Classification Search
CPC .. A61B 19/52; A61B 19/5244; A61B 19/54; A61B 2017/00694; A61B 2017/00699; A61B 2019/448; A61B 2019/5251; A61B 2019/547; A61N 5/1049; A61N 5/1067
USPC ............... 600/427, 595; 340/572.4
See application file for complete search history.

(56) References Cited

U.S. PATENT DOCUMENTS

| 6,144,875 | A  | * | 11/2000 | Schweikard et al. | ......... 600/427 |
| 6,731,970 | B2 | * | 5/2004 | Schlossbauer et al. | ...... 600/428 |
| 6,734,795 | B2 |   | 5/2004 | Price | |
| 6,753,783 | B2 |   | 6/2004 | Friedman et al. | |
| 6,759,959 | B2 |   | 7/2004 | Wildman | |
| 6,853,303 | B2 |   | 2/2005 | Chen et al. | |
| 6,861,954 | B2 |   | 3/2005 | Levin | |
| 6,954,148 | B2 |   | 10/2005 | Pulkkinen et al. | |
| 6,961,000 | B2 |   | 11/2005 | Chung | |
| 6,985,870 | B2 | * | 1/2006 | Martucci et al. | ................. 705/3 |
| 6,998,541 | B2 |   | 2/2006 | Morris et al. | |
| 7,019,650 | B2 |   | 3/2006 | Volpi et al. | |
| 7,030,761 | B2 | * | 4/2006 | Bridgelall et al. | ......... 340/572.2 |
| 7,061,381 | B2 |   | 6/2006 | Forcier et al. | |
| 7,075,434 | B2 |   | 7/2006 | Shafir | |
| 7,098,793 | B2 |   | 8/2006 | Chung | |

(Continued)

*Primary Examiner* — Katherine Fernandez
(74) *Attorney, Agent, or Firm* — Avery N. Goldstein; Blue Filament Law PLLC

(57) ABSTRACT

A system is provided for subject movement compensation during a medical procedure. The system uses passive radiofrequency identification tags associated with a subject, and at least one active RFID reader is positioned to interrogate the position of at least three such passive radiofrequency identification tags so as to triangulate the geometric position of a subject body tissue. The reader generates an output signal corresponding to a distance between said reader and a tag. A microprocessor calculates a displacement of a tag relative to the reader from said output signal to yield a value corresponding to subject movement. A medical device operates in synchronicity with the calculation corresponding to subject movement to compensate for subject movement during a treatment process in essentially real time. A process for subject movement compensation during a medical procedure is also provided.

14 Claims, 2 Drawing Sheets

(56) References Cited

U.S. PATENT DOCUMENTS

| | | |
|---|---|---|
| 7,119,688 B2 | 10/2006 | Wildman |
| 7,142,118 B2 | 11/2006 | Hamilton et al. |
| 7,154,378 B1 | 12/2006 | Ertas et al. |
| 7,158,030 B2 | 1/2007 | Chung |
| 7,158,754 B2 | 1/2007 | Anderson |
| 7,199,719 B2 * | 4/2007 | Steinberg .................. 340/572.8 |
| 7,218,232 B2 | 5/2007 | DiSilvestro et al. |
| 7,323,992 B2 * | 1/2008 | Doan et al. ................ 340/572.4 |
| 7,524,274 B2 * | 4/2009 | Patrick et al. ..................... 600/1 |
| 2002/0145526 A1 | 10/2002 | Friedman et al. |
| 2002/0158751 A1 | 10/2002 | Bormaster |
| 2002/0196150 A1 | 12/2002 | Wildman |
| 2003/0006878 A1 | 1/2003 | Chung |
| 2003/0189488 A1 | 10/2003 | Forcier et al. |
| 2004/0092815 A1 * | 5/2004 | Schweikard et al. ......... 600/425 |
| 2004/0100384 A1 | 5/2004 | Chen et al. |
| 2004/0158146 A1 * | 8/2004 | Mate et al. .................. 600/427 |
| 2004/0174261 A1 | 9/2004 | Volpi et al. |
| 2004/0212504 A1 | 10/2004 | Forcier et al. |
| 2005/0012617 A1 | 1/2005 | DiSilvestro et al. |
| 2005/0035862 A1 | 2/2005 | Wildman et al. |
| 2005/0073415 A1 | 4/2005 | Shafir |
| 2005/0088304 A1 | 4/2005 | Hines et al. |
| 2005/0110640 A1 | 5/2005 | Chung |
| 2005/0280536 A1 | 12/2005 | Hamilton et al. |
| 2006/0006999 A1 * | 1/2006 | Walczyk et al. ......... 340/539.27 |
| 2006/0033623 A1 | 2/2006 | Hines et al. |
| 2006/0043177 A1 | 3/2006 | Nycz et al. |
| 2006/0066453 A1 | 3/2006 | Homanfar et al. |
| 2006/0077040 A1 | 4/2006 | Bormaster |
| 2006/0079764 A1 * | 4/2006 | Wright et al. ................. 600/431 |
| 2006/0093089 A1 * | 5/2006 | Vertatschitsch et al. ....... 378/65 |
| 2006/0109118 A1 | 5/2006 | Pelo et al. |
| 2006/0119481 A1 | 6/2006 | Tethrake et al. |
| 2006/0142656 A1 | 6/2006 | Malackowski et al. |
| 2006/0145856 A1 | 7/2006 | Tethrake et al. |
| 2006/0145871 A1 | 7/2006 | Donati et al. |
| 2006/0173291 A1 | 8/2006 | Glossop |
| 2006/0180647 A1 * | 8/2006 | Hansen ........................ 235/375 |
| 2006/0181421 A1 | 8/2006 | Forcier et al. |
| 2006/0187044 A1 | 8/2006 | Fabian et al. |
| 2006/0202827 A1 | 9/2006 | Volpi et al. |
| 2006/0214791 A1 | 9/2006 | Tethrake et al. |
| 2006/0232407 A1 | 10/2006 | Ballard |
| 2006/0232408 A1 | 10/2006 | Nycz et al. |
| 2006/0241396 A1 | 10/2006 | Fabian et al. |
| 2006/0241399 A1 | 10/2006 | Fabian |
| 2006/0244593 A1 | 11/2006 | Nycz et al. |
| 2006/0244597 A1 | 11/2006 | Tethrake et al. |
| 2006/0264742 A1 | 11/2006 | Neubauer et al. |
| 2006/0291621 A1 * | 12/2006 | Yan et al. ....................... 378/65 |
| 2007/0030152 A1 | 2/2007 | Sprague |
| 2007/0035383 A1 | 2/2007 | Roemerman et al. |
| 2007/0066888 A1 | 3/2007 | Maschke |
| 2007/0083111 A1 | 4/2007 | Hossack et al. |
| 2007/0090951 A1 | 4/2007 | Chan et al. |
| 2007/0093709 A1 | 4/2007 | Abernathie |

* cited by examiner

US 9,498,647 B2

FIDUCIAL MARKER SYSTEM FOR SUBJECT MOVEMENT COMPENSATION DURING MEDICAL TREATMENT

FIELD OF THE INVENTION

The present invention in general relates to non-optical fiducial markers deployed as part of a system for subject movement during a medical treatment and in particular, to a fiducial marker system that compensates for subject movement in real time.

BACKGROUND OF THE INVENTION

The delivery of high intensity radiation to cancerous body tissue with a highly focused delivery is complicated by subject movement during the radiation administration session. While bolting a subject skull into a frame has proven to be partially successful, cervical flexion and respiration still contributes to radiation delivery defocus. While anesthesia has proven partly successful in compensating for cervical flexion and respiration, the difficulties and possible complications associated with anesthesia make this an unattractive option.

Treatment of a lesion located in the thoracic or abdominal cavity exacerbates the problem associated with patient movement. With a diaphragm traveling about 10 cm in an adult human, dynamic positional change of organs is observed during a respiration cycle. The result of organ movement is a radiation delivery defocus with tissue surrounding a lesion being subjected to unintended dosing.

Prior art attempts to address physiological movement during radiation dosing have met with limited success. Typical of these systems is the establishment of a camera array around the three-dimensional subject volume. A series of blinking lights secured to subject skin are tracked by the cameras and through geometric triangulation, the location of a surgical tool, catheter tip, or fiducial marker is noted. However, owing to the slow speed associated with such a system, the scans are typically performed prior to a surgical procedure or during an interruption in the procedure and, as such, lack real-time responsiveness needed for radio-dosing. A variation on such a system uses reflective spheres secured to the subject with pulsing lights proximal to the cameras in order to approximate volume through triangulation. These methodologies have met with limited acceptance owing to the inability of the optical system to simultaneously detect a fiducial marker or medical instrument internal to the subject volume while computing volume changes associated with respiratory physiology.

A more sophisticated prior art approach to this problem achieves a five second lag time relative to subject motion and is available under the trade name CyberKnife®. This method uses a series of magnetic resonance imaging or computed-aided tomography images to compute hundreds of planar x-ray images prior to a procedure. The procedure occurs on a fluoroscopy table with fluoroscopy images being compared by a computer to the computed x-ray images to ascertain biplanar fluoroscopy image pattern match with the computed x-ray images so as to determine subject position. This process has met with limited acceptance owing to a five second lag being a considerable time period as compared to a respiratory cycle. Additionally, a subject must be semi-restrained in order to derive a therapeutic effect.

To further improve the compensation for respiratory physiology, a constellation of radio-opaque fiducials are implanted within the subject volume that is to be the subject of the therapy and the procedure repeated of collecting MRI or CT scans from which biplanar x-ray images are derived prior to a therapeutic session. The computed biplanar x-rays are compared with fluoroscope images collected prior to or during a procedure, which still further reduces the lag time during the computed respiratory cycle position and the actual body position. While a constellation of fiducials made up of skin marks or markers placed on the chest wall afford a timing of respiratory physiology-related movement, a time lag still persists.

Thus, there exists a need for a fiducial marking system capable of calculating a target movement within a subject related to subject movement on a greater precision than has been heretofore available. Additionally, there exists a need for a fiduciary marking system capable of predicting periodic subject movement so as to further define radiation dosing.

SUMMARY OF THE INVENTION

A system is provided for subject movement compensation during a medical procedure. The system uses passive radiofrequency identification tags associated with a subject, and at least one active RFID reader is positioned to interrogate the position of at least three such passive radiofrequency identification tags so as to triangulate the geometric position of a subject body tissue. The reader generates an output signal corresponding to a distance between said reader and a tag. A microprocessor calculates a displacement of a tag relative to the reader from said output signal to yield a value corresponding to subject movement. A medical device operates in synchronicity with the calculation corresponding to subject movement to compensate for subject movement during a treatment process in essentially real time.

A process for subject movement compensation during a medical procedure is also provided. The process involves scanning a subject to compute a vectoral distance between a passive radiofrequency identification tag secured to the subject and a target tissue within the subject. The vectoral distance is stored in a digital memory accessible by a microprocessor. A radiofrequency reader is then activated to generate an output signal corresponding to a distance between the tag and the reader. A microprocessor then computes a position of the target tissue based on the output signal, with the coordinates of the target tissue being communicated to a medical device by way of the output signal.

DESCRIPTION OF THE INVENTION

The present invention has utility in compensating for subject movement during the course of a medical procedure. The present invention achieves a superior movement compensation scheme through the application of passive radiofrequency identification tags (RFIDs). Through the implantation or skin adherence of multiple fiducial RFID markers, the movement of a subject is measured with shorter time intervals as compared to the prior art, or even continuously.

As a result, radiotherapy treatments are delivered with greater efficacy and less incidental exposure of surrounding tissues.

At least one RFID fiducial marker is implanted or otherwise secured in a fixed positional relationship relative to a target. As the present invention monitors target position through triangulation, the present invention in its simplest embodiment implants a passive RFID tag in proximity to the target and monitors the position of the RFID tag and therefore the target through triangulation signal intercept by two active radiofrequency readers. It is appreciated that while two readers monitoring a single RFD tag affords displacement information in a plane defined by the two readers and the RFID tag, the inclusion of a third reader outside of this plane affords three-dimensional displacement information. While the theory and the practice of distance monitoring between a passive RFID tag and an RFID reader are well known, in brief, with a known interrogation frequency emitted from the reader, the time after which a return signal is received from the RFID tag is directly proportional to the distance therebetween.

Alternatively, an inventive system implants or otherwise secures multiple passive RFID tags to a subject as fiducial markers in the general area of the target. A multi-channel reader or multiple readers of single or multi-channel design calculates the relative position of the constellation of RFID fiducial markers and through vector geometry, the position of the target. Preferably, multiple markers define a triangle about a target tissue. More preferably, four or more markers bound a target tissue to define a tetrahedron. It is appreciated that target positional correlation relative to a fiducial marker is facilitated by calculating movement ranges associated with extreme positions associated with a respiratory cycle.

Figure 1:
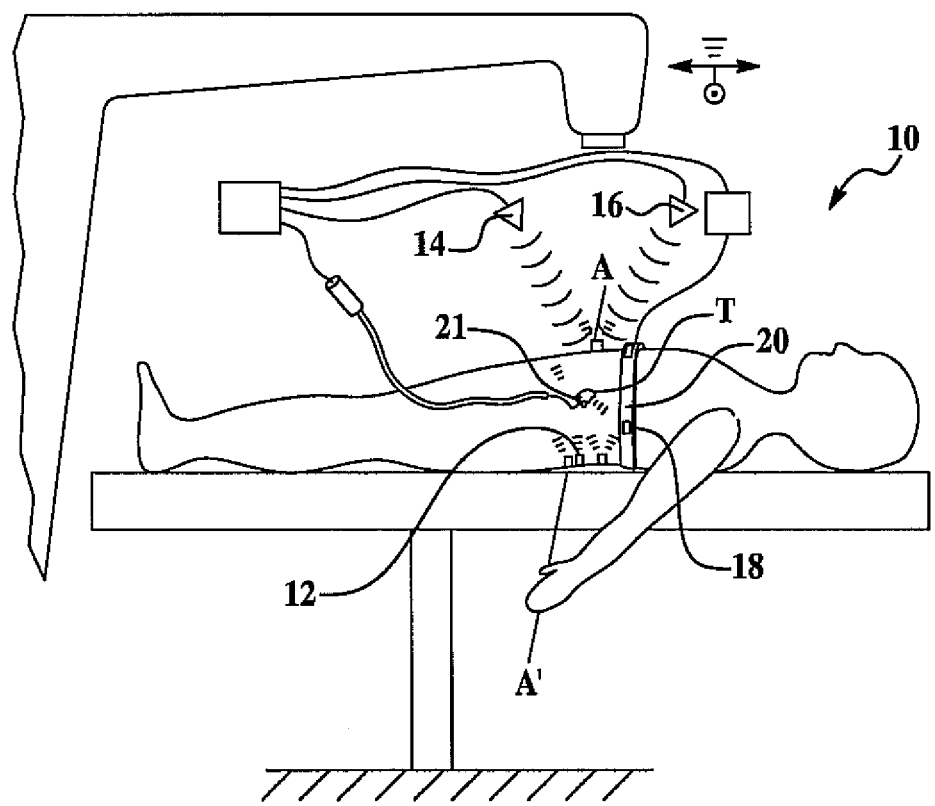
FIG. 1 is a partial cutaway perspective view of an inventive fiducial marker system for calculating positional changes in a subject.
Figure 2:
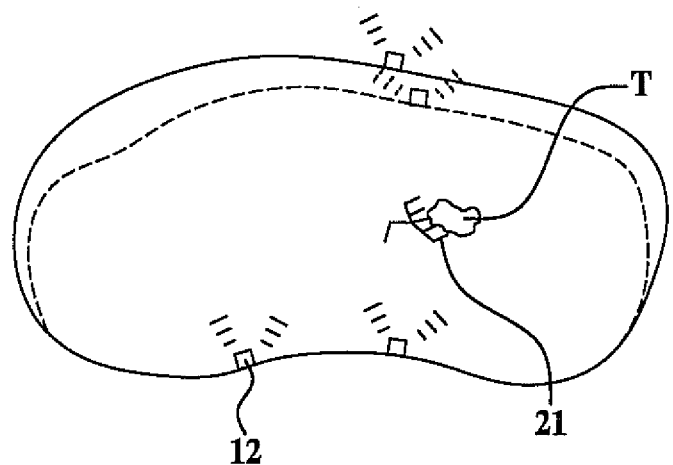
FIG. 2 is a transverse planar view along the axis A-A' of FIG. 1.

Referring now to FIGS. 1 and 2, the inventive system is depicted generally at 10. A system 10 has at least one passive RFID fiducial marker 12 positioned relative to a target mass T while a subject rests on a treatment platform 13. It is appreciated that a marker 12 placed adjacent to, or within a target T, is sufficient to measure the position of target T in three dimensions with at least two readers 14 and 16 exterior to the subject. Fiducial markers 18 according to the present invention optionally decorate an elastomeric belt 20 adapted to secure about the thoracic or abdominal cavity of an individual. Through a simultaneous reading of the movement of fiducial markers 18 decorating the belt 20, it is possible to accurately predict whether the chest cavity of a subject will continue to expand or deflate based on measurement of one or more previous breathing cycles. Additionally, in instances where a radioactive seed is threaded by a catheter into an individual, optionally, an inventive RFID fiducial marker 21 is secured proximal to the seed or catheter tip.

Optionally, upon completion of at least one full respiratory cycle, predictive coordinate data is fed to the radiation source based on the period and chest cavity expansion associated with a prior respiratory cycle so as to afford a regular motion of the radiation source. Such predictive positional data is updated by actual measured positional signal from the reader. The use of a belt 20 is appreciated to facilitate predictive movements based on the respiratory cycle.

Owing to the small dimensions of an RFID tag, typically on the order to tens to hundreds of microns, and the exogenous nature of the tag requires an inventive tag to be encapsulated with a biocompatible coating. Suitable coatings for an RFID fiducial tag illustratively include surgically implantable polymers, such as polyesters, such as nylon; fluoropolymers, such as perfluoroalkalenes; metals, such as titanium; and combinations thereof. It is appreciated that the exact placement of a given RFID fiducial tag is immaterial so long as the dynamic vectoral separations between a given marker and a target are known throughout the course of a given subject movement, such as a respiratory cycle.

Figure 3:
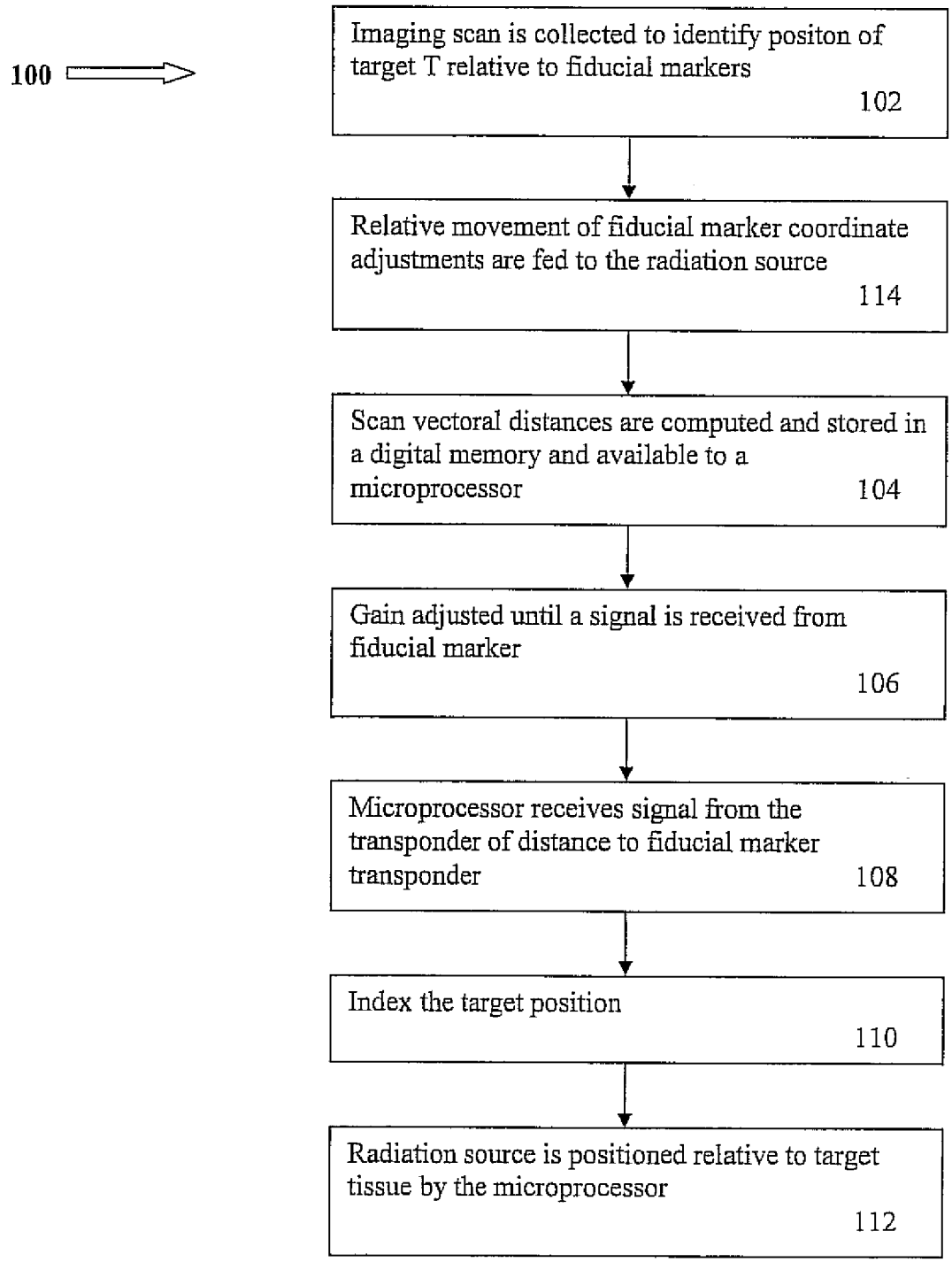
FIG. 3 is a schematic block diagram of procedural steps according to the present invention.

Referring now to FIG. 3, the inventive process of monitoring subject movement in the course of a medical procedure is depicted generally at 100. The implantation or a fixation of multiple fiducial markers in a subject, an imaging scan 102 is collected to identify position of target T relative to the markers. Imaging scans are collected as MRI or CT scans. From the scans, vectoral distances between markers and a target mass are computed. The vectoral distances are stored in a digital memory and made available to a microprocessor 104. With a subject placed on a treatment platform as depicted in FIG. 1, a reader external to the subject is activated, the gain adjusted until a signal is received from fiducial marker 106.

The microprocessor having access to the vectoral distances between markers and target receives an electronic signal from the reader distance measurements between each fiducial marker and a reader 108. A baseline position is determined by comparing a reader signal to the vectoral distances stored in the digital memory 104 and serves to index the target position 110. A radiation source is positioned relative to the target tissue through provision of coordinate data 112 from the microprocessor. Radiation sources are those known in the art and include synchrotrons, cathode ray tubes, and robotic arms carrying radioactive sources. Subsequent movement of the subject, whether the motion is translational, rotational or respirational, is then compensated for based on the relative movement of each fiducial marker and radiation source coordinate adjustments are fed to the radiation source 114.

As an alternate to movement of a radiation source relative to a target, it is appreciated that the microprocessor instead controls a radiation source shutter, such that radiation is only emitted from the source onto the target upon coincidence between the target and a fixed radiation source.

By way of example, compared to a fixed reader, a parallel distance displacement of all responding fiducial markers is indicative of subject translation, such as that associated with sliding onto a treatment platform. Motion of distant markers towards a reader, as depicted in FIGS. 1 and 2, towards the fixed reader while more proximal fiducial markers become more distant by an approximately equal amount is indicative of subject rotation. Movement of an abdominal or thoracically mounted fiducial marker relative to the lumbar of fixed marker is associated with respiration. It is appreciated that actual data collected from a reader, while predominantly corresponding to a respiratory mode, often has rotational or translational mode components, especially as a radiation session continues and subject muscles are required to retain a particular position begin to fatigue. As a radiofrequency reader is capable of collecting thousands of data points relating to the position of each fiducial marker per second, and matrix algebra to compute the position of a target can occur on a gigahertz time scale, effective real-time translation of a radiation source is provided to maintain exposure cross-section of the target.

Patents and publications mentioned in the specification are indicative of the levels of those skilled in the art to which the invention pertains. These patents and publications are incorporated herein by reference to the same extent as if each individual patent or publication was explicitly and individually incorporated herein by reference.

One skilled in the art will readily appreciate that the present invention is described herein with specific examples representative of preferred embodiments. Changes with respect to the present invention and other uses therefor will occur to those skilled in the art. These changes are encompassed within the spirit of the invention as defined by the scope of the appended claims.

The invention claimed is:

1. A system for subject movement compensation during a medical procedure performed using a medical device, the system comprising:
    a treatment platform for supporting a subject during the medical procedure;
    a first set of at least one fixed passive radiofrequency identification (RFID) tag, where said at least one fixed RFID tag is adapted to be secured in a fixed positional relationship relative to a target related to the subject;
    a second set of a plurality of passive RFID tags secured to an elastomeric belt for encompassing the subject and positioned above the treatment platform, where said elastomeric belt is adapted to be secured to an exterior surface of the subject;
    a plurality of RFID readers positioned to interrogate said at least one fixed RFID tag and said second set of the plurality of passive RFID tags secured to said elastomeric belt, said plurality of RFID readers configured to generate a set of output signals corresponding to respective distances between said plurality of RFID readers and each of said at least one fixed RFID tags and said plurality of passive RFID tags secured to said elastomeric belt and wherein said plurality of RFID readers are further configured to interrogate said first set and said second set of RFID tags successively at short time intervals or continuously;
    a microprocessor configured to calculate based on said set of output signals displacements of said at least one fixed passive RFID tag and said second set of the plurality of passive RFID tags secured to said elastomeric belt to yield a value corresponding to subject movement that is translational, rotational, or respirational after one or more breathing cycles is made and configured to feed coordinate adjustments determined based on said value to said medical device; and
    wherein said medical device is configured to continuously move during the medical procedure with respect to a position of said target in synchronicity with said microprocessor calculation corresponding to the value of subject movement, wherein said plurality of RFID readers are secured to a portion of said medical device that is configured to be continuously controlled in real-time during the medical procedure in response to the coordinate adjustments from said microprocessor without interrupting or delaying the performance of the medical procedure.

2. The system of claim 1, wherein said first set comprises at least three fixed RFID tags which define a triangle in relation to the subject, the subject encompassing the target.

3. The system of claim 1, further comprising at least one additional passive RFID tag wherein said at least one additional passive RFID tag is for implanting in an interior of the said-subject.

4. The system of claim 1, wherein said first set and said second set of RFID tags are at least four RFID tags defining a tetrahedron encompassing a target tissue.

5. The system of claim 1, wherein said plurality of RFID readers maintain a fixed position.

6. The system of claim 1, wherein said microprocessor calculates the displacements through triangulation.

7. The system of claim 1, further comprising at least one additional passive RFID tag wherein said at least one additional passive RFID tag is secured proximal to a radioactive seed or to a catheter tip during said medical procedure.

8. The system of claim 1, wherein said plurality of RFID readers has a gain adjusted until a signal is received from said plurality of passive RFID tags secured to said elastomeric belt and said at least one fixed passive RFID tag.

9. A process for subject movement compensation during a medical procedure performed using a medical device, the process comprising:
    providing a plurality of passive belt radiofrequency identification (RFID) tags secured to an elastomeric belt;
    attaching said elastomeric belt to encompass the subject at a position proximal to a target tissue of the subject;
    attaching at least one passive body radiofrequency identification (RFID) tag to an exterior surface of the subject in opposition to said plurality of passive belt RFID tags, where said plurality of passive belt RFID tags secured to said elastomeric belt and said at least one passive body RFID tag attached to the exterior surface of the subject serve as fiducial markers;
    reading the plurality of passive belt RFID tags and said at least one passive body RFID tag attached to the subject, who is resting on a treatment platform during the medical procedure, with a plurality of RFID readers positioned above the treatment platform, to compute respective distances between said plurality of RFID readers and each of said plurality of passive belt RFID tags and said at least one passive body RFID tag attached on the subject, wherein said reading is done successively at short time intervals or continuously and wherein said plurality of RFID readers generate an output signal or signals based on said computation of said respective distances;
    calculating with a microprocessor a position of said target tissue based on said output signal or signals in relation to stored vectoral distances between the target and said fiducial markers, where the microprocessor further calculates displacement of said plurality of passive belt RFID tags or said at least one passive body RFID tag based on said output signal or signals to yield a value corresponding to subject movement and based on one or more previous breathing cycles a prediction of subject movement is made;
    communicating, from said microprocessor to the medical device above the subject, coordinates for positioning said medical device based on the calculated position of said target tissue; and
    adjusting the position of said medical device continuously during the medical procedure with respect to the position of said target tissue to maintain synchronicity with subject movement, wherein said plurality of RFID readers are secured to a portion of said medical device that is configured to move continuously during the medical procedure in response to coordinate adjustments determined based on the value corresponding to subject movement from said microprocessor without interrupting or delaying the performance of the medical procedure.

10. The process of claim 9, further comprising the step of opening a shutter in response to the communicated coordinates.

11. The process of claim 9, wherein said at least one passive body RFID tag comprises of at least three passive body RFID tags which define a triangle in relation to the subject, the subject encompassing the target tissue.

12. The process of claim 9, further comprising: predicting coordinate data of the position of the target tissue relative to said plurality of passive belt RFID tags secured proximal to the tissue based on the period and chest cavity expansion associated with a prior respiratory cycle; and feeding to said medical device said predicted coordinate data.

13. The process of claim 12, further comprising updating the predicted coordinate data with the output signal or signals.

14. The process of claim 9, wherein said plurality of RFID readers has a gain adjusted until a signal is received from the fiducial markers.

\* \* \* \* \*